United States Patent [19]

Eastman et al.

[11] Patent Number: 5,347,067
[45] Date of Patent: Sep. 13, 1994

[54] ALKYLATION CATALYST REGENERATION

[75] Inventors: Alan D. Eastman; Ronald G. Abbott, both of Bartlesville, Okla.

[73] Assignee: Phillips Petroleum Company, Bartlesville, Okla.

[21] Appl. No.: 119,861

[22] Filed: Aug. 24, 1993

Related U.S. Application Data

[62] Division of Ser. No. 904,938, Jun. 26, 1992, Pat. No. 5,276,245.

[51] Int. Cl.$^5$ .............................................. C07C 2/62
[52] U.S. Cl. .................................... 585/724; 585/723; 585/730; 585/823
[58] Field of Search ............... 585/823, 723, 724, 730

[56] References Cited

U.S. PATENT DOCUMENTS 5,276,245 1/1994 Eastman et al. .................... 585/724

Primary Examiner—Asok Pal
Attorney, Agent, or Firm—Charles W. Stewart

[57] ABSTRACT

Described is a novel acid-soluble oil composition produced as a by-product from an alkylation reaction catalyzed by a sulfone-containing catalyst. Also described is a novel process for regenerating an alkylation catalyst which contains a sulfone component. The regeneration process utilizes alumina adsorbent to remove a substantial portion of the hydrogen halide from the spent catalyst, thereby producing a neutralized stream, which is then treated with carbon to remove a substantial portion of the reaction by-product to produce a sulfone stream substantially free of reaction by-product and hydrogen halide.

10 Claims, 2 Drawing Sheets

ALKYLATION CATALYST REGENERATION

This application is a division of application Ser. No. 07/904,938, filed Jun. 26, 1992, now U.S. Pat. No. 5,276,245.

The present invention relates to the regeneration of a catalyst composition utilized in a hydrocarbon conversion process. More particularly, the invention, relates to the regeneration of a catalyst mixture, comprising a sulfone compound and a hydrogen halide compound, utilized in the alkylation of olefin hydrocarbons by isoparaffin hydrocarbons.

BACKGROUND OF THE INVENTION

It has recently been discovered that a mixture, comprising a sulfone compound and a hydrogen halide compound, is an effective catalyst for use in the alkylation of olefin hydrocarbons by isoparaffin hydrocarbons to produce an alkylate reaction product, or alkylate. This discovery has been disclosed or claimed, or both, in several patent applications such as application Ser. No. 07/877,336 of Abbott and Randolph, filed May 1, 1992, and application Ser. No. 07/877,338 of Abbott et al, filed May 1, 1992. The alkylate reaction product generally contains hydrocarbons having seven or more carbon atoms, and it is a highly desirable gasoline blending component because of its high octane value as a motor fuel.

While a process which utilizes a catalyst composition comprising a sulfone component and a hydrogen halide component produces an alkylate product of very high quality, one side effect from using such a process in the production of alkylate is the formation of certain polymeric reaction by-products such as those referred to as acid-soluble oils, or ASO. These polymeric reaction by-products are referred to as acid-soluble oils because they are soluble in the catalyst utilized in the alkylation process; and thus remain in the catalyst phase when the alkylate product resulting from the contact of a hydrocarbon mixture with an alkylation catalyst is separated from the alkylation catalyst. In an alkylation process which continuously separates the catalyst phase from the alkylation reaction product for reuse in the process reaction zone, there is a buildup of ASO in the catalyst. Over time the ASO concentration will reach unacceptable concentration levels if not removed. A low concentration of ASO in the alkylation catalyst comprising a sulfone component and a hydrogen halide component is believed to have a beneficial effect upon the alkylation process or its product. However, higher concentrations of ASO in the alkylation catalyst have an adverse effect upon the catalyst activity and the final alkylate end-product. An ASO concentration in the alkylation catalyst that exceeds certain acceptable limits will result in lowering the octane of the alkylate end-product with incremental increases in the ASO concentration causing incremental decreases in the alkylate octane.

In conventional alkylation processes that use hydrogen fluoride (HF) as a catalyst, as opposed to the use of the aforementioned novel catalyst comprising a sulfone component and a hydrogen halide component, there are certain known methods used to remove the ASO from the HF catalyst used in a continuous alkylation process. Particularly, enough of a portion of the HF catalyst that is utilized in the alkylation process is treated, or regenerated, so as to remove an amount of ASO at a rate that approximates the rate of accumulation of ASO in the alkylation catalyst. This is done by passing a portion of the HF catalyst to a stripping vessel whereby the HF is stripped from the ASO by means of a vaporous hydrocarbon such as isobutane with the HF passing as a part of the vaporous overhead stream from the stripping vessel and the ASO passing as a bottoms stream from the stripping vessel for further processing.

While the conventional alkylation catalyst regeneration techniques have worked well in the regeneration of the conventional HF catalyst, conventional means cannot be used to regenerate an alkylation catalyst mixture which includes a sulfone component, This is because the boiling range of ASO overlaps the boiling temperatures of certain sulfones such as sulfolane, Therefore, simple distillation techniques as are used to separate HF from ASO cannot be used to effectively regenerate a sulfone-containing alkylation catalyst. Additionally, it is necessary to separate ASO from the sulfone in order to reclaim the sulfone for reuse as a catalyst in the alkylation process.

SUMMARY OF THE INVENTION

It is, therefore, an object of this invention to provide a novel process for the regeneration of alkylation catalysts.

A further object of this invention is to provide a process for the removal of ASO from alkylation catalysts containing a sulfone component.

A still further object of this invention is to provide a novel acid-soluble oil composition produced as a reaction by-product from an alkylation process that utilizes a catalyst containing a sulfone component.

Thus, the process of the present invention relates to the alkylation of olefin hydrocarbons by paraffin hydrocarbons by utilizing a catalyst mixture that includes a sulfone component. A sulfone-containing mixture comprising a sulfone and ASO is contacted with an adsorbent material suitable for the removal of at least a portion of the ASO component of the sulfone-containing mixture.

The composition of the present invention is an acid-soluble oil produced as a reaction by-product in an alkylation process comprising the step of contacting a hydrocarbon mixture, comprising olefins and isoparaffins, with a catalyst mixture, comprising a sulfone component and a hydrogen halide component.

Figure 1:
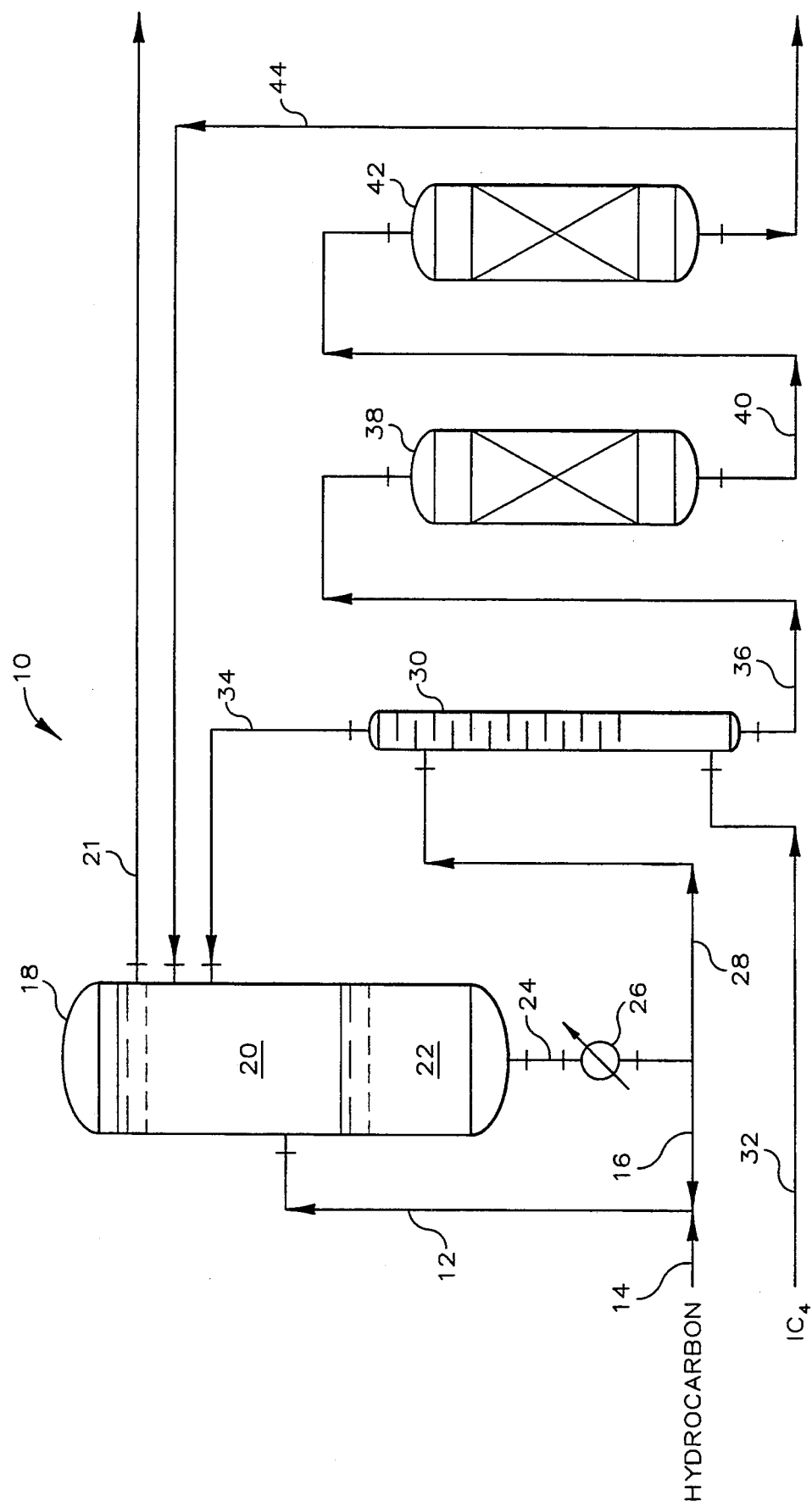
FIG. 1 provides schematic representation of the process which is one embodiment of the invention.

Other objects and advantages of the invention will be apparent from the foregoing detailed description of the invention and the appended claims.

DETAILED DESCRIPTION OF THE INVENTION

The novel acid soluble oil composition of the present invention is produced as a reaction by-product in an alkylation process comprising the step of contacting a hydrocarbon mixture, which comprises olefins and isoparaffins, with an alkylation catalyst, which comprises, consists of, or consists essentially of a hydrogen halide component and a sulfone component. As referred to within this description and in the claims, the term "acid soluble oil" or "ASO" means those conjunct polymers which are highly olefinic oils produced by acid-catalyzed reactions of hydrocarbons. An extensive description and characterization of certain types of conjunct polymer oils is provided in the *Journal of Chemical and Engineering Data* article entitled "Molecular Structure of Conjunct Polymers" pages 150-160, Volume 8, Number 1, by Miron and Lee. This article is incorporated herein by reference. The physical properties of ASO depend upon the particular hydrocarbon feed processed, the catalyst, utilized in the process, feed contaminants such as hydrogen sulfide, butadiene, oxygenates and other compounds, and the alkylation process reaction conditions. Thus, as the term is used herein, ASO will be those conjunct polymers produced as a by-product in the catalyzed reaction of mono-olefins with isoparaffins utilizing a catalyst mixture comprising, consisting of, or consisting essentially of a sulfone component and a hydrogen halide component. The preferred mono-olefins for use in the catalyzed reaction are those having from three to five carbon atoms and the preferred isoparaffins are those having from four to six carbon atoms. The preferred sulfone component is sulfolane and the preferred hydrogen halide component is hydrogen fluoride.

The ASO by-product derived from the hydrocarbon reaction catalyzed by a sulfone-containing alkylation catalyst can further be generally characterized as having a specific gravity, with water at 60° F. as the reference, in the range of from about 0.8 to about 1.0, an average molecular weight in the range of from about 250 to about 350, and a bromine number in the range of from about 40 to about 350.

The hydrogen halide component of the catalyst composition or catalyst mixture can be selected from the group of compounds consisting of hydrogen fluoride (HF), hydrogen chloride (HCl), hydrogen bromide (HBr), and mixtures of two or more thereof. The preferred hydrogen halide component, however, is hydrogen fluoride, which can be utilized in the catalyst composition in anhydrous form; but, generally, the hydrogen fluoride component utilized can have a small amount of water. In a catalyst composition including hydrogen fluoride and sulfolane, the amount of water present in no event can be more than about 30 weight percent of the total weight of the hydrogen fluoride component, which includes the water. Preferably, the amount of water present in the hydrogen fluoride component is less than about 10 weight percent. Most preferably, the amount of water present in the hydrogen fluoride component is less than 7 weight percent. When referring herein to the hydrogen halide component, or more specifically to the hydrogen fluoride component, of the catalyst composition of the invention, it should be understood that these terms mean that the hydrogen halide component is ether an anhydrous mixture or a non-anhydrous mixture. The references herein to weight percent water contained in the hydrogen halide component means the ratio of the weight of water to the sum weight of the water and hydrogen halide multiplied by a factor of 100 to place the weight ratio in terms of percent.

The sulfones suitable for use in this invention are the sulfones of the general formula

R—SO$_2$—R′ wherein R and R′ are monovalent hydrocarbon alkyl or aryl substituents, each containing from 1 to 8 carbon atoms. Examples of such substituents include dimethylsulfone, di-n-propylsulfone, diphenylsulfone, ethylmethylsulfone and the alicyclic sulfones wherein the SO$_2$ group is bonded to a hydrocarbon ring. In such a case, R and R′ are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures.

The alkylation catalyst used in the alkylation process wherein an ASO reaction by-product is produced can comprise, consist of, or consist essentially of a hydrogen halide component as described herein add a sulfone component as described herein. Preferably, the ASO by-product will be produced in an alkylation process in which the hydrocarbon mixture is contacted with an alkylation catalyst having sulfolane as its sulfone component and hydrogen fluoride as its hydrogen halide component. In the case where the alkylation catalyst comprises sulfolane and hydrogen fluoride, good alkylation results can be achieved with weight ratio of hydrogen fluoride to sulfolane in the alkylation, catalyst in the range of from about 1:1 to about 40:1. A preferred weight ratio of hydrogen fluoride to sulfolane can range from about 2.3:1 to about 19:1 and, more preferably, it can range from 3:1 to 9:1.

To obtain the by-product ASO from an alkylation reaction effluent or product, any suitable means can be used to separate the by-product ASO from the alkylate product. One example of such suitable separation means is the allowance of a phase separation between the alkylation catalyst and the alkylate product, which is generally a mixture of highly branched paraffin hydrocarbons, other paraffin hydrocarbons and alkylate followed by the removal of ASO from the alkylation catalyst phase. Any suitable means can be used to recover the ASO from the alkylation catalyst.

In order to improve selectivity of the alkylation reaction of the present invention toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 120° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40-90 volume percent catalyst phase and about 60-10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

The alkylation process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants may be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. As described herein, a portion of the catalyst can be continuously regenerated or reactivated by any suitable treatment and returned to the alkylation reactor.

One embodiment of this invention includes a process for removing ASO from a sulfone-containing mixture comprising the step of contacting a sulfone-containing mixture, comprising a sulfone component and ASO, with an adsorbent material suitable for the removal of at least a portion of the ASO component of said sulfone-containing mixture to produce a treated sulfone-containing mixture. The adsorbent material can be those materials described herein and can be selected from the group consisting of alumina, carbon, and mixtures thereof. Preferably, the sulfone component of the sulfone-containing mixture is sulfolane. The ASO component of the sulfone-containing mixture can be present in an amount no more than about 20 weight percent of the sulfone component. Preferably, the concentration of ASO is less than 15 weight percent of the sulfone component, and most preferably, the ASO will be present at a concentration of less than 10 weight percent. The treated sulfone-containing mixture will have a reduced concentration of ASO, generally being less than 2 weight percent of the sulfone-containing mixture. Preferably, the ASO will be present in an amount less than 1 weight percent, and most preferably, the ASO will be present in an amount less than 0.1 weight percent.

Another embodiment of the process of this invention contemplates the resolution of problems associated with the regeneration of sulfone-containing alkylation catalyst mixtures by the removal of at least a portion of the ASO contained within such mixtures, The accumulation of ASO in sulfone-containing alkylation catalysts occurs when an alkylation process continuously reuses its catalyst. In a continuous alkylation process, the ASO reaction by-product will build up in the catalyst until, if not removed, it reaches unacceptable concentration levels that can have negative effects upon the catalyst performance and, ultimately, the alkylation product quality. It is generally desirable to maintain the concentration of ASO in the sulfone-containing alkylation catalyst at no more than about 20 weight percent of the catalyst with the weight percent ASO being based upon the total weight of the catalyst mixture exclusive of the ASO component. Preferably, the concentration of the ASO in the sulfone-containing alkylation catalyst is less than about 15 weight percent, and most preferably, the concentration of ASO is less than 10 weight percent. There may be some process advantages in maintaining a low concentration of ASO in the sulfone-containing catalyst mixture, but it is believed that an ASO concentration exceeding about 10 weight percent of the catalyst will have a detrimental effect upon the catalyst performance.

Thus, in order to maintain the catalytic activity of a sulfone-containing alkylation catalyst mixture, the catalyst must be processed to remove at least a portion of the ASO contained within such catalyst. To achieve this, the sulfone-containing alkylation catalyst mixture is contacted with an adsorbent material so as to remove at least a portion of the ASO component of the sulfone-containing alkylation catalyst mixture. It is noted that it is generally desirable to have at least a portion of the hydrogen halide component of the sulfolane-containing alkylation mixture removed prior to contacting the resultant sulfone-containing mixture, which comprises a sulfone component, a hydrogen halide component, and ASO, with the adsorbent material to thereby remove at least a portion of the ASO component. Therefore, the sulfone-containing mixture will be the sulfone-containing alkylation catalyst mixture having at least a portion of the hydrogen halide component removed. Any suitable method can be used to separate the hydrogen halide component from the sulfone-containing alkylation catalyst mixture, such as, for example, flash separation, distillation, extraction, stripping, and other suitable separation methods. One preferred method is by stripping means for separating the sulfone-containing alkylation catalyst mixture into an overhead stream, comprising a major portion of the hydrogen halide component of the sulfone-containing alkylation catalyst, and a bottoms stream, comprising the sulfone-containing mixture, with the use of vaporous butane, which is preferably isobutane, as the stripping agent.

Generally, the concentration of the hydrogen halide component in the sulfone-containing mixture will be less than about 10 weight percent of the mixture with the weight percent determined by the weight fraction of the hydrogen halide to the sum total weight of hydrogen halide and sulfone multiplied by a factor of 100 to yield a percent. Because it is very difficult to remove the entire amount of hydrogen halide from the mixture, the lower limit of hydrogen halide concentration from a practical standpoint can approach about 0.1 weight percent, but, preferably, the concentration can be less than 0.1 weight percent. Thus, the concentration range of hydrogen halide in the mixture can range from about 0.1 weight percent to about 10 weight percent. Preferably, however, the concentration can range from about 0.1 to about 7.5 weight percent, and most preferably, it can range from 0.1 to 5.0 weight percent.

Generally, the adsorbent material contemplated by this invention can be contained within a vessel defining a contacting zone in which the sulfone-containing mixture can be contacted with the adsorbent material. However, this invention is not confined to the use of standard vessels for defining a contacting zone, but any suitable means known in the art can be utilized for contacting the sulfone-containing mixture with the adsorbent material.

The adsorbent material utilized to remove ASO from the sulfone-containing mixture can be any adsorbent that can either suitably or effectively remove at least a portion of the ASO component contained in such mixture. Preferably, the adsorbent material is selected from the group consisting of alumina, carbon and mixtures thereof.

The carbon adsorbent material can be any activated carbon material that is suitable for use as contemplated by this invention and for the selective removal of at least a portion of the ASO component contained in the sulfone-containing mixture. The activated carbon adsorbent can be characterized by its large specific surface area which can range from about 300 $m^2/g$ to about 2500 $m^2/g$ as determined by the American Society for Testing Materials (ASTM) Standard Test Method D3663-84 entitled "Standard Test Method for Surface Area of Catalysts". The standard ASTM test D3663-84 is incorporated herein and made a part hereto by reference. Also, the activated carbon adsorbent can further be characterized by its pore diameter which can range from about 10 $\mu m$ to about 50 $\mu m$ as determined by the method of mercury intrusion prosimetry described by ASTM Standard Test D4284-88 entitled "Standard Test Method for Determining Pore Volume Distribution of Catalysts by Mercury Intrusion Porosimetry". The standard ASTM test D4284-88 is incorporated herein and made a part hereto by reference. It is generally desirable to use commercially available activated carbon. One such suitable commercially available activated carbon, for example, is the product known by its tradename as Calgon Filtrasorb 400, which is manufactured and marketed by Calgon Carbon Corporation.

The alumina adsorbent material can be any alumina suitable for use as contemplated by this invention and for the selective removal of at least a portion of the ASO component contained in the sulfone-containing mixture or for use as a neutralizing agent for the removal of at least a portion of the hydrogen halide component of a sulfone-containing stream. Such suitable aluminas include, for example, a variety of the commercially available activated aluminas and calcined aluminas. Generally, the alumina material will have a surface area in the range of from about 150 $m^2/g$ to about 500 $m^2/g$ as determined by ASTM D3663-84. Also, the pore diameter of the alumina material can range from about 25 $\mu m$ to about 125 $\mu m$ as determined by ASTM D4284-88. It is generally desirable to use commercially available aluminas. One such suitable commercially available alumina is the product known by its tradename HF-200 manufactured and marketed by Alcoa. The most preferred alumina for use in this invention is a calcined alumina having a gamma crystalline structure, also known as gamma-alumina, and other aluminas, such as chi-alumina having surface areas greater than about 50 $m^2/g$.

The process conditions under which a sulfone-containing mixture is contacted with an adsorbent composition can be any conditions that are suitable or effective for removing at least a portion of the concentration of ASO from the alkylation catalyst mixture. The removal efficiency of the adsorbent material is not believed to be highly dependent upon the contact pressure because the adsorption phenomenon is thought to be the result of a liquid-solid interaction; however, the process pressure should exceed about 0.5 atmospheres of absolute pressure and can range upwardly to about 30 atmospheres, or more, of absolute pressure. The more common operating pressure will generally range from about atmospheric pressure to about 200 pounds per square inch of gauge pressure (psig).

As for the contacting temperature, any suitable temperature can be utilized that provides for an effective removal of at least a portion of the ASO from the sulfone-containing mixture. Generally, the upper and lower temperature limits are set by the physical characteristics of the mixture being treated and the physical characteristics of the ASO contained in such mixture. Considering the lower temperature limit, pure sulfolane has a melting point of about 81.3°–82.0° F., but when sulfolane is in the form of a mixture with water and hydrogen fluoride, the melting point is significantly lower. Therefore, the lower limit for the contacting temperature approximates 0° F. As for the upper temperature limit, it is determined by such factors as the initial boiling temperature of the ASO and the temperature at which the sulfone component of the mixture begins to thermally decompose. Thus, the upper contacting temperature approximates 400° F. Therefore, the contact temperature generally will range from about 0° F. to about 400° F. Preferably, the contacting temperature will range from about 50° F. to about 350° F., and most preferably, it will range from 60° F. to 325° F.

Figure 2:
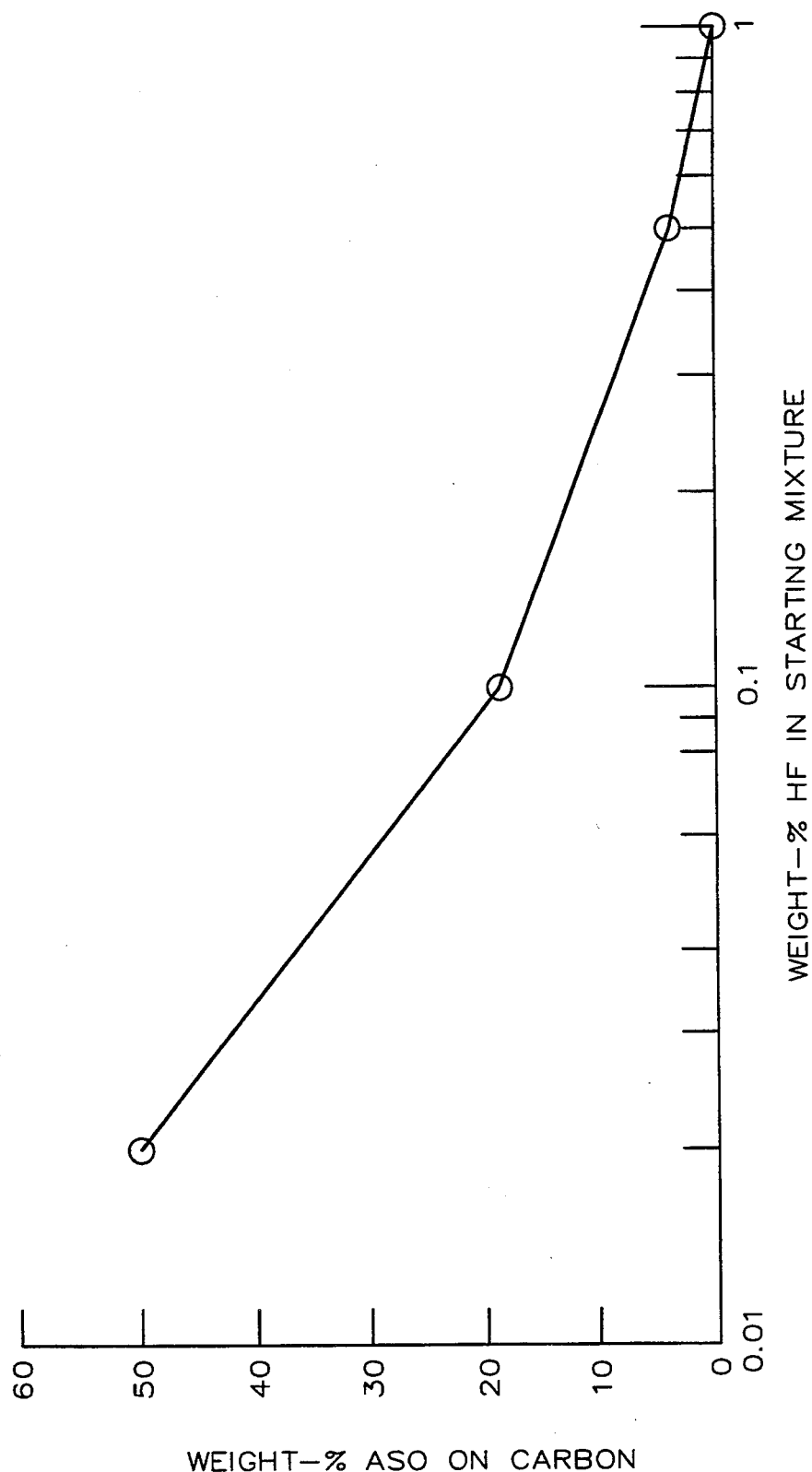
FIG. 2 is a plot demonstrating the capacity of an activated carbon to adsorb ASO from a sulfone-containing mixture as a function of the weight percent HF contained in such mixture.

It has been determined that in the process of removing ASO from a sulfone-containing mixture the presence of even a small concentration of a hydrogen halide compound, particularly hydrogen fluoride, in the catalyst has the effect of reducing the ability of an activated carbon adsorbent to selectively remove ASO from the mixture. As illustrated by the data presented in FIG. 2, a small concentration of hydrogen fluoride in the sulfone-containing mixture being contacted with an activated carbon material can have the effect of essentially rendering the carbon ineffective in ASO removal. Thus, one important, and potentially critical, aspect of this invention is for an ASO contaminated sulfone-containing mixture to be substantially free of a concentration of hydrogen halide or, more generally, for the ASO contaminated sulfone-containing mixture to be neutralized prior to, or concurrently with, contacting the mixture with a carbon material. Any means suitable for the removal of at least a portion of a concentration of hydrogen halide from an ASO contaminated sulfone-containing mixture or composition can be used. Alternatively, any neutralizing agent suitable for the removal of at least a portion of the hydrogen halide contained in an ASO contaminated sulfone-containing mixture can be used. Examples of such suitable neutralizing agents can include, but are not limited to, basic hydroxides, such as those of alkali and alkaline earth metals, e.g., KOH, Ca(OH)$_2$, and NaOH; basic oxides, such as zinc oxide and tin oxide; and amphoteric oxides, such as aluminum oxide. Preferred neutralizing agents can include the various types of aluminas and hydroxide compounds. The most preferred neutralizing material is gamma-alumina.

As earlier described herein, it is desirable for the hydrogen halide component of the ASO contaminated sulfone-containing alkylation catalyst mixture to be minimized before contacting the resultant sulfone-containing mixture with a neutralizing agent. In particular, when a significant portion of the sulfone-containing alkylation catalyst mixture comprises hydrogen halide; for instance, when the weight ratio of hydrogen halide to sulfolane is in the range of from about 1:1 to about 40:1, it is preferable for a major portion of the hydrogen halide to be removed from the catalyst mixture to give a sulfone-containing mixture or a recovered catalyst mixture. This sulfone-containing mixture or recovered catalyst mixture can comprise, consist of, or consist essentially of a sulfone component, a hydrogen halide component, and ASO. Generally, the concentration of the hydrogen halide component in the recovered catalyst mixture will be less than about 10 weight percent of the catalyst mixture with the weight percent determined by the weight fraction of the hydrogen halide to total weight of hydrogen halide and sulfone multiplied by a factor of 100 to yield a percent. Because it is very difficult to remove the entire amount of hydrogen halide from the catalyst mixture, the lower limit of hydrogen halide concentration can approach about 0.1 weight percent, but, preferably, the lower concentration limit of hydrogen halide can be less than 0.1 weight percent. Thus, the concentration range of hydrogen halide in the recovered catalyst mixture can range from about 0.1 weight percent to about 10 weight percent. Preferably, however, the concentration can range from about 0.1 to about 7.5 weight percent, and most preferably, it can range from 0.1 to 5.0 weight percent.

As for the use of the neutralizing agent or neutralizing material, the recovered catalyst mixture, having a concentration of hydrogen halide, is contacted with the neutralizing material to thereby remove a significant portion of the hydrogen halide component of the recovered catalyst mixture to produce a neutralized sulfone-containing mixture. The neutralized sulfone-containing mixture will be significantly free of hydrogen halide; and, generally, it will have a concentration of less than about 2.0 weight percent. Preferably, the neutralized sulfone-containing catalyst mixture will have a concentration of less than about 1.0 weight percent, and most preferably, it will have less than 0.1 weight percent hydrogen halide.

The neutralization of the recovered catalyst mixture or the sulfone-containing mixture will permit further processing or treatment of the neutralized sulfone-containing mixture to remove at least a portion of the ASO component not removed during the neutralization step. A significant portion of the ASO component of the neutralized catalyst is removed by contacting it with an adsorbent material suitable for removing a significant portion of the ASO component contained therein to produce a regenerated catalyst mixture or a treated sulfone-containing mixture. The ASO component of the regenerated catalyst mixture or the treated sulfone-containing mixture will, in most instances, be present in a concentration of less than about 2 weight percent of the total weight of the sulfone component. Preferably, the weight percent of ASO present in the treated sulfone-containing mixture can be less than about 1.0, and most preferably, the ASO will be present in an amount less than 0.1 weight percent. The regenerated catalyst mixture or treated sulfone-containing mixture can be reused as a portion of a sulfone-containing alkylation catalyst mixture comprising, consisting of, or consisting essentially of a sulfone and a hydrogen halide.

Now referring to FIG. 1, there is depicted by schematic representation an alkylation process 10. A hydrocarbon feed mixture, comprising olefins and isoparaffins, is introduced into reactor-riser 12 through conduit 14. Reactor-riser 12 defines a reaction zone wherein the hydrocarbon mixture is contacted, or admixed, with a catalyst mixture, comprising sulfolane and hydrogen fluoride, in order to produce a reaction product and a reaction by-product. The olefins of the hydrocarbon feed mixture generally comprise one or more olefins having from three to five carbon atoms, and the isoparaffins of the hydrocarbon feed mixture generally will have from four to six carbon atoms. The catalyst mixture is introduced into reactor-riser 12 via conduit 16. The admixture of hydrocarbon feed mixture and catalyst mixture passes through the reaction zone defined by reactor-riser 12 wherein a reaction takes place in which the olefins of the hydrocarbon feed mixture react with isoparaffins of the hydrocarbon feed mixture to produce an alkylate reaction product. Also, within the reaction zone, the reaction by-product, ASO, is formed. The reaction effluent from reactor-riser 12 passes to settler vessel 18, which defines a separation zone for separating the alkylate reaction product from the catalyst mixture to produce a separated reaction product 20 and a separated catalyst mixture 22. The separated catalyst mixture 22 will contain a substantial amount of the alkylation reaction by-product, ASO. The separated reaction product 20 passes to downstream processing via conduit 21. The separated catalyst mixture 22 can be recycled via conduits 24 and 16 to reactor-riser 12 for reuse as the alkylation catalyst mixture. Interposed in conduit 24 is catalyst cooler 26, which defines a heat transfer zone for exchanging heat from separated catalyst mixture 22 to a heat transfer fluid such as water.

At least a portion, sometimes referred to as a slip stream or a drag stream, of the separated catalyst mixture 22 passes by way of conduit 28 to stripping column 30, which defines a separation zone for separating the slip stream of separated catalyst mixture 22 into an overhead stream, comprising a major portion of the hydrogen fluoride contained in the slip stream, and a bottoms stream, comprising a major portion of the sulfolane component of the slip stream. The bottoms stream will also contain a major portion of the reaction by-product, ASO, contained in the slip stream. Introduced by way of conduit 32 is vaporous isobutane for stripping the hydrogen fluoride from the slip stream. The overhead stream passes by way of conduit 34 to settler vessel 18 where the hydrogen fluoride is recombined with the separated catalyst mixture 22 for reuse, and the stripping isobutane is combined with the separated reaction product 20.

The bottoms stream from stripping column 30 passes by way of conduit 36 to first contacting vessel 38, which contains an adsorbent material and defines a separation zone for removing by adsorption or by neutralization of a substantial port,on of the hydrogen fluoride contained in the bottoms stream to produce a neutralized bottoms stream.

The neutralized bottoms stream then passes through conduit 40 to second contacting vessel 42, which contains an adsorbent material and defines a separation zone for removing a substantial portion of the ASO contained in the neutralized bottoms stream to produce a regenerated catalyst, or sulfolane stream, that is substantially free of ASO and hydrogen fluoride. This sulfolane stream passes through conduit 44 to settler vessel 18 where it is remixed with separated catalyst mixture 22 for reuse as the sulfolane component of the alkylation catalyst mixture.

The following examples demonstrate the advantages of the present invention. These examples are by way of illustration only, and are not intended as limitations upon the invention as set out in the appended claims.

EXAMPLE I

An ASO by-product derived from the hydrocarbon reaction catalyzed by a catalyst mixture of sulfolane and HF was obtained to determine some of its physical properties. The catalyst mixture used in the hydrocarbon reaction contained a weight ratio of HF to sulfolane of about 1.5, and the hydrocarbon charge included isobutane and 2-butenes (60% trans, 40% cis isomers) with a molar ratio of isobutane to 2-butenes of about 11. The reaction temperature was about 90° F., and the reaction pressure was about 90 psig. Table I presents certain physical properties, including a distillation, of the resultant ASO obtained from the hydrocarbon reaction.

TABLE I

Distillation of the ASO derived from hydrocarbon reaction catalyzed by a sulfolane/HF catalyst mixture and other physical properties of the ASO.

| Temperature °F. | Volume % of Sample | Bromine Number of Fraction |
| --- | --- | --- |
| 70–200 | 19 | 51 |
| 200–210 | 8 | 45 |
| 210–225 | 18 | 56 |
| 225–250 | 15 | 58 |
| >250 | 40 | 59 |
| Bromine Number of ASO | 32 | |
| API Gravity (60° F.) | 37.1 | |
| Specific Gravity (60° F.) | 0.8391 | |

EXAMPLE II

This Example II describes generally the experimental method used to obtain data relating to the adsorption properties of carbon, alumina, and mixtures thereof and the neutralization properties of alumina.

The general experimental procedure for testing the use of the materials of carbon or alumina, or both, in the recovery of ASO from a sulfolane-containing mixture of sulfolane and ASO included the use of a glass cylinder of approximately one inch in diameter and from 12 inches to 24 inches in length. Placed in the bottom of the cylinder was either glass wool or glass beads to provide support for the active material, and on top of the active material was placed either glass beads or glass wool to assist in providing an even distribution of the sulfolane-containing mixture over the active material. Heat was optionally provided to the glass cylinder to induce the flow of the sulfolane-containing mixture through the bed of active material. The sulfolane-containing mixture had a weight ratio of sulfolane-to-ASO of approximately 9 to 1. The color of the resultant filtrate provided an indication as to when the adsorption capacity of the active material was spent and thus was monitored to determine when the experiment was complete.

EXAMPLE III

This Example III illustrates the unexpected relationship between the capacity of activated carbon to adsorb ASO from a sulfolane-containing mixture of sulfolane and ASO as a function of the concentration of hydrogen fluoride in the sulfolane-containing mixture.

The experimental method used to obtain the data presented in Table II is substantially similar to that described in Example II. Various concentrations of hydrogen fluoride in the sulfolane-containing mixture were established before contacting the mixture with an activated carbon material. The data obtained are presented in Table II, which unexpectedly demonstrates that the level of acid concentration in the sulfolane-containing mixture has a large impact upon the ASO adsorption capacity of activated carbon. These data are also plotted in FIG. 2.

TABLE II

The capacity of activated carbon to adsorb ASO from a sulfolane-containing mixture, having a ratio of sulfolane to ASO of 9 to 1, as a function of HF concentration.

| Concentration of HF in sulfolane-containing Mixture Weight % HF | Adsorption Capacity of Carbon Weight % ASO on Carbon |
| --- | --- |
| 0.02 | 50 |
| 0.10 | 19 |
| 0.50 | 4 |
| 1.00 | Nil |

EXAMPLE IV

This Example IV demonstrates that various commercially available aluminas can suitably be used to remove HF from a sulfolane-containing mixture of sulfolane and ASO, either by adsorption or by neutralization. Also, this example demonstrates that alumina can also adsorb a portion of the ASO contained in the sulfolane-containing mixture as well as perform a neutralization function.

The experimental method used to obtain the data presented in Table III is substantially similar to that described in Example II with the exceptions that the pH of effluent from the cylinder was monitored to determine when the neutralization capacity of the alumina was used up and the sulfolane-containing mixture was provided with a 5 weight percent concentration of HF. The data presented in Table III demonstrate that various commercially available aluminas can suitably be used to neutralize a sulfolane-containing mixture with some adsorption of ASO prior to contacting the thus-neutralized mixture with an activated carbon material.

TABLE III

The capacity of various aluminas to neutralize and remove ASO from a sulfolane-containing mixture having a weight ratio of sulfolane to ASO of 9 to 1.

| Alumina Type | Neutralization Capacity (meq* HF/g) | ASO Adsorption Capacity (mg/g) |
|---|---|---|
| LaRoche Alumina A-202 | 1.8 | 50 |
| Alcoa Alumina HF-200 | 5.0 | 150 |
| Engelhard Activated Bauxite "Sure cat" | 1.3 | 35 |
| LaRoche SAS Alumina | 4.1 | 120 |

*meq represents millequivalents

While this invention has been described in terms of the presently preferred embodiment, reasonable variations and modifications are possible by those skilled in the art. Such variations and modifications are within the scope of the described invention and the appended claims.

That which is claimed is:

1. An alkylation process, comprising the steps of:
  (a) contacting a hydrocarbon mixture, comprising olefins and isoparaffins, with a catalyst mixture, comprising sulfolane and HF, within a reaction zone to thereby produce a reaction product and a reaction by-product;
  (b) separating said reaction product from said catalyst mixture within a first separation zone to produce a separated reaction product and a separated catalyst mixture with said separated catalyst mixture containing a substantial amount of said reaction by-product;
  (c) utilizing said separated catalyst mixture as at least a portion of said catalyst mixture;
  (d) passing a portion of said separated catalyst mixture to a second separation zone to thereby separate said a portion of said separated catalyst mixture into a second separation zone overhead stream, comprising a major portion of the HF component of said a portion of said separated catalyst mixture, and a second separation zone bottoms stream comprising a major portion of the sulfolane component of said a portion of said separated catalyst mixture and a major portion of the reaction by-product component of said a portion of said separated catalyst mixture;
  (e) utilizing said second separation zone overhead stream as at least a portion of the HF component of said catalyst mixture;
  (f) contacting said second separation zone bottoms stream with alumina to thereby remove a substantial portion of the HF contained in said second separation zone bottoms stream to produce a neutralized second separation zone bottoms stream;
  (g) contacting said neutralized second separation zone bottoms stream with carbon to thereby remove a substantial portion of said major portion of the reaction by-product to produce a sulfolane stream substantially free of said reaction by-product and HF; and
  (h) utilizing said sulfolane stream as at least a portion of the sulfolane component of said catalyst mixture.

2. An alkylation process comprising the steps of:
  (a) contacting a hydrocarbon mixture, comprising olefins and isoparaffins, with a catalyst mixture, comprising a sulfone component and a hydrogen halide component, within a reaction zone to thereby produce a reaction product and a reaction by-product;
  (b) separating said reaction product from said catalyst mixture within a first separation zone to produce a separated reaction product and a separated catalyst mixture with said separated catalyst mixture containing a substantial amount of said reaction by-product;
  (c) passing said separated catalyst mixture to a second separation zone to thereby separate said separated catalyst mixture into a second separation zone overhead stream, comprising a major portion of the hydrogen halide component of said separated catalyst mixture, and a second separation zone bottoms stream, comprising a major portion of the sulfone component of said separated catalyst mixture and a major portion of the reaction by-product component of said separated catalyst mixture;
  (d) contacting said second separation zone bottoms stream with alumina to thereby remove a substantial portion of the hydrogen halide contained in said second separation zone bottoms stream to produce a neutralized second separation zone bottoms stream; and
  (e) contacting said neutralized second separation zone bottoms stream with carbon to thereby remove a substantial portion of said major portion of the reaction by-product to produce a sulfone stream substantially free of said reaction by-product and said hydrogen halide component.

3. A process as recited in claim 1, further comprising: utilizing said separated catalyst mixture as at least a portion of said catalyst mixture.

4. A process as recited in claim 2, further comprising: utilizing said second separation zone overhead stream as a portion of the hydrogen halide component of said catalyst mixture.

5. A process as recited in claim 3, further comprising: utilizing said sulfone stream as at least a portion of the sulfone component of said catalyst mixture.

6. A process as recited in claim 5, wherein the sulfone component of said catalyst mixture is sulfolane and the hydrogen halide component of said catalyst mixture is hydrogen fluoride.

7. A process as recited in claim 6, wherein said reaction by-product comprises acid soluble oil.

8. A process as recited in claim 7, wherein the weight ratio of hydrogen halide to sulfone in said catalyst mixture is in the range of from about 1:1 to about 40:1 wherein the acid soluble oil in said catalyst mixture is present in an amount no more than about 20 weight percent of said catalyst mixture.

9. A process as recited in claim 8, wherein said sulfone stream contains acid soluble oil at a concentration less than about 2 weight percent of the total weight of the sulfone component.

10. A process as recited in claim 9, wherein the contact pressure of contacting steps (d) and (e) of claim 1 is in the range of from 0.5 atmospheres of absolute pressure to about 30 atmospheres of absolute pressure and the contact temperature of contacting steps (d) and (e) of claim 1 is in the range of from 0° F. to about 400° F.

* * * * *